US007838271B2

(12) United States Patent
Robins et al.

(10) Patent No.: US 7,838,271 B2
(45) Date of Patent: Nov. 23, 2010

(54) MICROBIOLOGICAL METHOD FOR PRODUCING AMIDES

(75) Inventors: Karen Tracey Robins, South Guangzhou (CN); Toru Nagasawa, Kurono (JP)

(73) Assignee: Lonza AG, Basel (CH)

( * ) Notice: Subject to any disclaimer, the term of this patent is extended or adjusted under 35 U.S.C. 154(b) by 611 days.

(21) Appl. No.: 11/710,983

(22) Filed: Feb. 27, 2007

(65) Prior Publication Data

US 2007/0148743 A1 Jun. 28, 2007

Related U.S. Application Data

(60) Division of application No. 10/465,495, filed on Jun. 19, 2003, now abandoned, which is a continuation of application No. PCT/EP02/00103, filed on Jan. 8, 2002.

(60) Provisional application No. 60/342,373, filed on Dec. 27, 2001.

(30) Foreign Application Priority Data

Jan. 9, 2001 (EP) .................................. 01100493

(51) Int. Cl.
*C12P 13/02* (2006.01)

(52) U.S. Cl. ..................................................... 435/129

(58) Field of Classification Search ....................... None
See application file for complete search history.

(56) References Cited

U.S. PATENT DOCUMENTS

| | | | | |
|---|---|---|---|---|
| 4,255,344 | A | 3/1981 | Imada et al. | |
| 4,432,887 | A | 2/1984 | Zajic et al. | |
| 4,720,456 | A | 1/1988 | Wagner et al. | |
| 5,179,014 | A | 1/1993 | Watanabe et al. | |
| 5,298,414 | A | 3/1994 | Bruce et al. | |
| 5,334,519 | A * | 8/1994 | Yamada et al. | 435/129 |
| 5,731,176 | A * | 3/1998 | Yamada et al. | 435/129 |
| 5,753,472 | A * | 5/1998 | Yamada et al. | 435/129 |
| 5,827,699 | A | 10/1998 | Yanenko | |
| 6,444,451 | B1 | 9/2002 | Robins et al. | |
| 6,699,695 | B1 * | 3/2004 | Matsuyama et al. | 435/129 |
| 7,105,322 | B2 * | 9/2006 | Robins et al. | 435/129 |

FOREIGN PATENT DOCUMENTS

| | | | |
|---|---|---|---|
| DE | 43 13 649 | C1 | 1/1995 |
| EP | 0 307 926 | A2 | 9/1988 |
| WO | WO 99/05306 | A1 | 2/1999 |

OTHER PUBLICATIONS

Wieser et al. "Low-molecular-mass nitrile hydratase from Rhodococcus rhodochrous J1: purification, substrate specificity and comparison with the analogous high-molecular-mass enzyme," FEMS Microbiology Letters, 1998, 169, 17-22.*

English translation of Japanese Office Action mailed Jan. 8, 2008, issued in connection with corresponding Japanese Patent Application No. 2002-556721.

JP 1990-000470, Jan. 5, 1990 (in Japanese)—equivalent to U.S. Patent No. 5,334,519.

Nagasawa et al, "Characterization of a new cobalt-containing nitrile hydratase purified from urea-induced cells of *Rhodococcus rhodochrous* J1", Eur. J. Biochem. 196, 581-589 (1991).

JP 61-162193, Jul. 22, 1986 (in Japanese)—equivalent to U.S. Patent No. 5,179,014.

Kato et al, "Nitrile hydratase involved in aldoxime metabolism from *Rhodococcus* sp. strain YH3-3", Eur. J. Biochem. 263, 662-670 (1999).

Sinolitsky et al, "Purification and Characterization of Nitrile Hydratase from *Rhodococcus rhodochrous* M8", Environmental Biotechnology: Principles of Applications, 1996, p. 96-104.

Langdahl BR, Bisp P, Ingvorsen K (1996), Nitrile hydrolysis by *Rhodococcus erythropolis* BL1, an acetonitrile-tolerant strain isolated from a marine sediment. Microbiology 142:145-154.

Nagasawa T, Mathew CD, Mauger J, Yamada H (1988), Nitrile Hydratase-Catalyzed Production of Nicotinamide from 3-Cyanopyridine in *Rhodococcus rhodochrous* J1, Applied and Environmental Microbiology 54(7):1766-1769.

Watanabe I, Satoh Y, Enomoto K (1987), Screening, Isolation and Taxonomical Properties of Mircroorganisms Having Acrylonitrile-hydrating Activity, Agric Biol Chem 51(12):3193-3199.

Asano Y, Fujishiro K, Tani Yoshiki, Yamada Hideaki (1982), Aliphatic Nitrile Hydratase from *Arthrobacter* sp. J-1 Purification and Characterization, Agric Biol Chem 45(5):1165-1174.

* cited by examiner

*Primary Examiner*—Christina Bradley
(74) *Attorney, Agent, or Firm*—Nixon & Vanderhye P.C.

(57) ABSTRACT

The present invention provides for microorganisms capable of tolerating acetonitrile concentrations of at least 3 M, enzyme extracts obtainable from these microorganisms, a nitrile hydratase obtainable from these microorganisms, a method for preparing amides using these microorganisms, the enzyme extracts or the nitrile hydratase obtainable therefrom, and a method for removing acetonitrile from solutions using these microorganisms, the enzyme extracts or the nitrile hydratase obtainable therefrom.

14 Claims, 11 Drawing Sheets

Figure 2: Temperature optimum
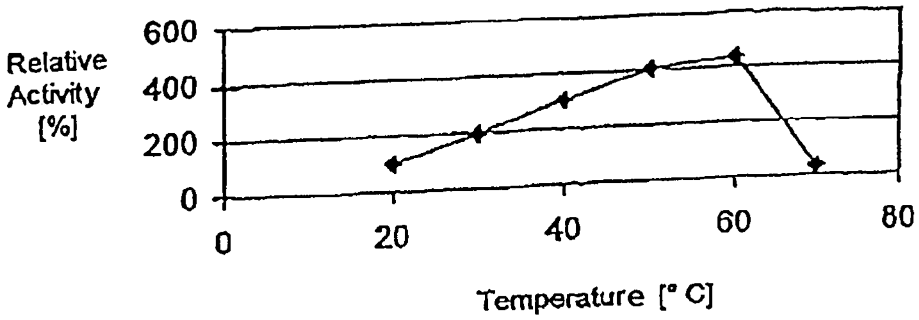
Figure 3: Thermal stability
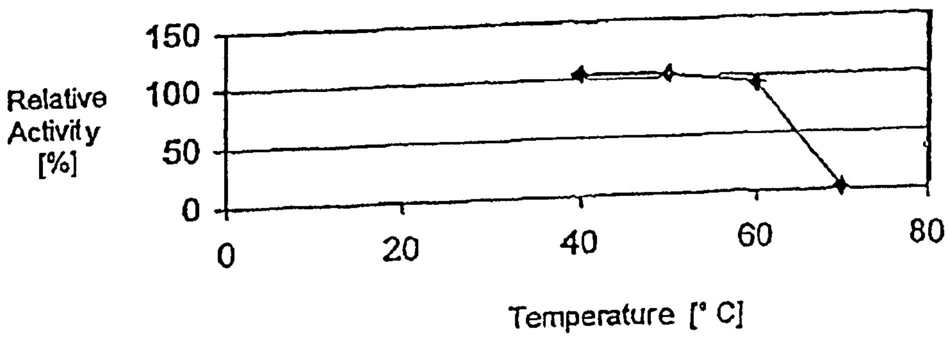

Figure 4: pH optimum
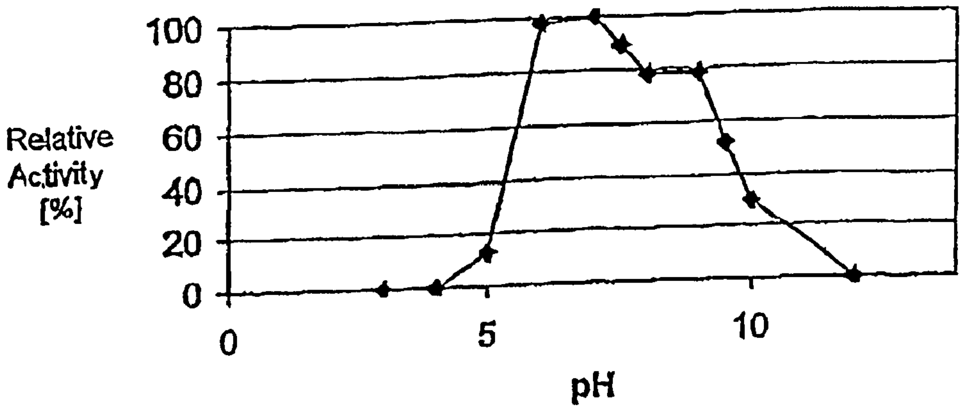
Figure 5: pH stability
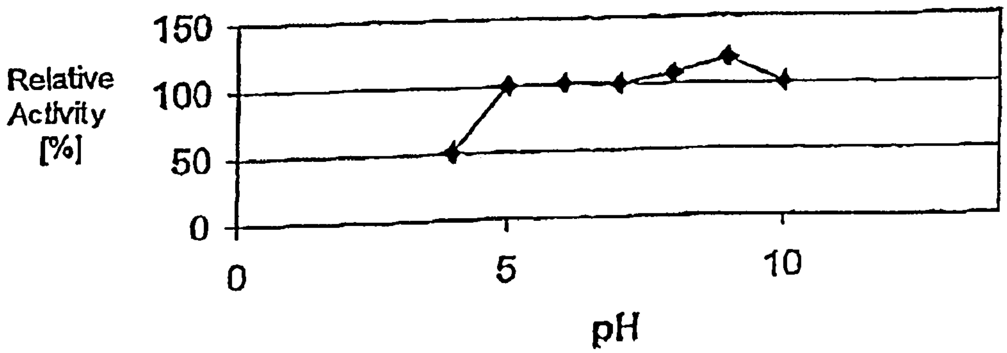

Figure 16: pH optimum
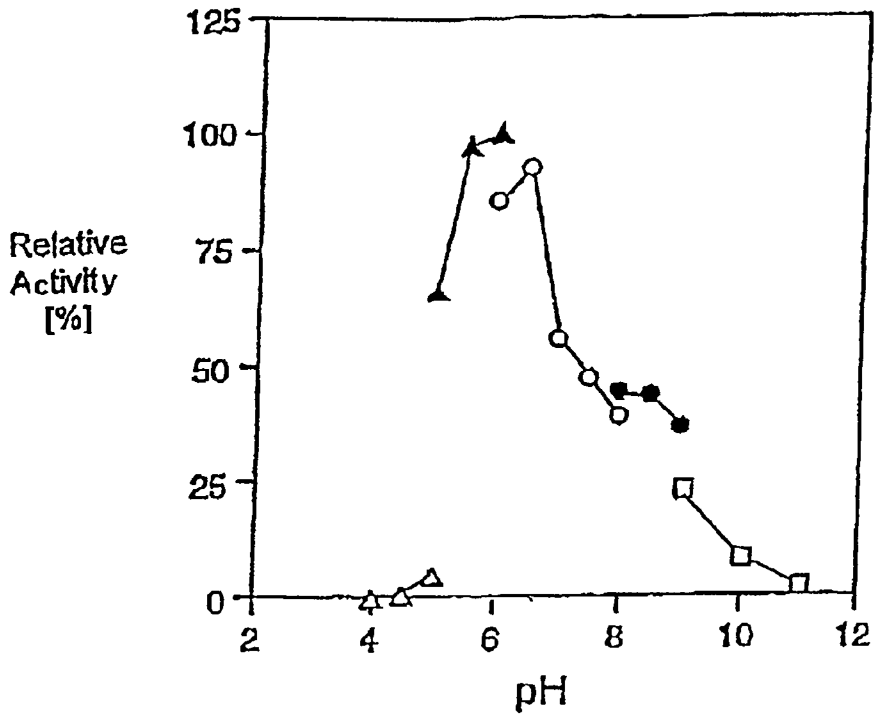
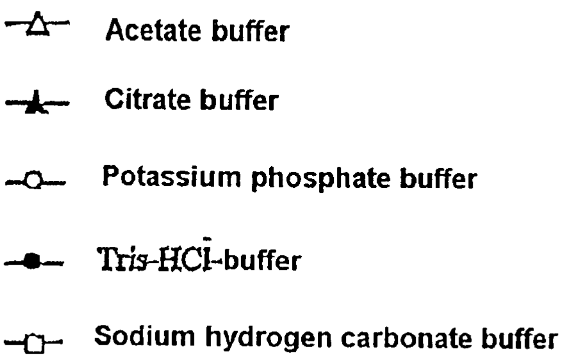

Figure 17: pH stability
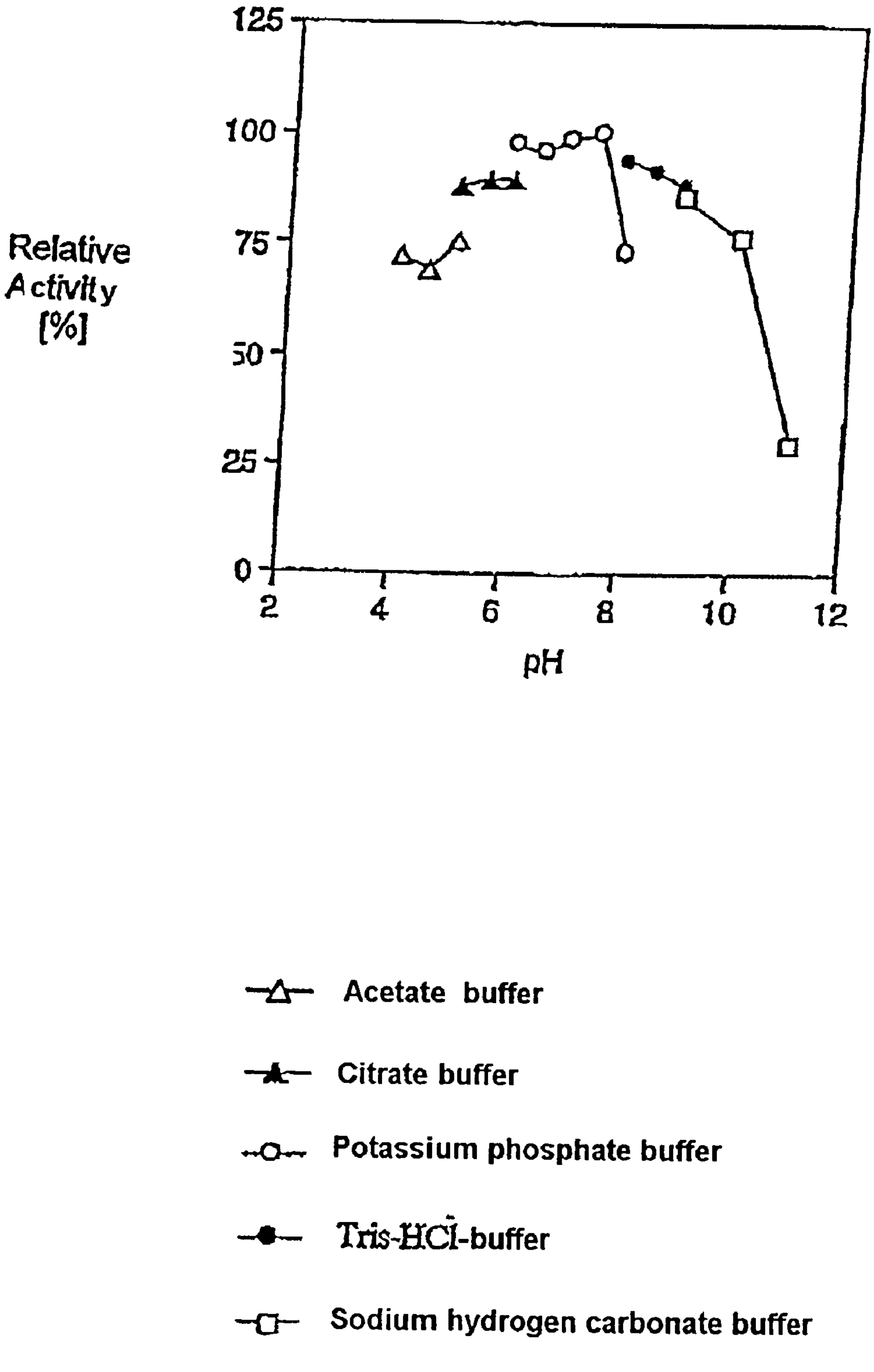

MICROBIOLOGICAL METHOD FOR PRODUCING AMIDES

CROSS-REFERENCE TO RELATED APPLICATIONS

This application is a divisional of application Ser. No. 10/465,495, filed Jun. 19, 2003 now abandoned, which is a continuation application of International Application No. PCT/EP02/00103, filed Jan. 8, 2002, which claims benefit of U.S. Provisional Application Ser. No. 60/342,373, filed Dec. 27, 2001 and European Patent Application No. EP 01100493.4, filed Jan. 9, 2001, the entire contents of each of which is hereby incorporated by reference in this application.

FIELD OF THE INVENTION

The invention relates to microorganisms which are capable of tolerating acetonitrile concentrations of at least 3 M, to an enzyme having nitrile hydratase activity, to a method for producing amides by using said microorganisms or said enzyme, and to the use of said microorganisms for removing acetonitrile waste.

A plurality of biotechnological methods for producing amides such as, for example, nicotinamide, a vitamin of the vitamin B complex, which is essential to animals and humans, are already known.

EP-A 0 307 926, for example, describes the conversion of 3-cyanopyridine to nicotinamide by means of *Rhodococcus rhodochrous* J1. This method has the disadvantage of *Rhodococcus rhodochrous* J1 being red, as a consequence of which the product is discolored. Furthermore, said microorganism has a high KM value with respect to the substrate 3-cyanopyridine, has low temperature tolerance and low tolerance with respect to 3-cyanopyridine.

WO 99/05306 describes, for example, a method for producing nicotinamide, starting from the corresponding nitrile, by means of microorganisms of the genera *Rhodococcus, Amycolatopsis* and *Actinomadura*. This method has the disadvantage that the microorganisms used, of the genus *Amycolatopsis*, are inactivated at elevated temperatures. Furthermore, said microorganisms have low tolerance to 3-cyanopyridine and nicotinamide. The described microorganisms of the genus *Rhodococcus* have a high $K_M$ value with respect to 3-cyanopyridine and low temperature stability. Accordingly, said method is not economical as an industrial process.

SUMMARY OF THE INVENTION

It was the object of the present invention to provide microorganisms which are relatively stable, have a relatively low $K_M$ value, for example for the substrate 3-cyanopyridine, and can therefore be used for a more economical method for producing amides, in which the corresponding amide can be isolated with very good yields and high purity.

This object is achieved by the microorganisms as claimed in claim 1, by the enzyme as claimed in claims 5 or 7, and by the method as claimed in claim 8. The microorganisms of the invention can be obtained by appropriate selection, for example from soil samples, sludge or wastewater, with the aid of common micro-biological techniques. Said microorganisms are conveniently selected by cultivation with a pyridinaldoxime of the general formula

I

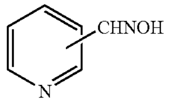

or with nitrites as carbon sources in the presence of cobalt ions and, for example, yeast extract and/or ammonium salts. This is followed by selecting from the cultures obtained those microorganisms which are capable of tolerating an acetonitrile concentration of at least 3 M and of converting nitrites such as, for example, 3-cyanopyridine and acetonitrile to the corresponding amide.

Pyridinaldoximes which may be used are pyridin-2-, pyridin-3- or pyridin-4-aldoxime.

Nitriles suitable for selection are in particular also those which are intended to be used as substrates in the later biotransformation, for example acetonitrile (acetic acid nitrile), propionitrile, butyronitrile, crotonic acid nitrile, adipic acid nitrile and malonic acid nitrile.

Preferred sources of the cobalt ions are “cobalt ion-generating cobalt compounds”, for example $Co^{2+}$ or $Co^{3+}$ salts such as cobalt chlorides, cobalt sulfates and cobalt acetates. The preferred cobalt compound used is a $Co^{2+}$ salt such as, for example, $CoC1_2$. However, cultivation may also be carried out in combination with metallic cobalt or with other cobalt compounds. Usually, cobalt or cobalt compounds are used in the cultivation medium in an amount of from 1 to 30 mg/l, preferably from 1 to 20 mg/l.

Examples of ammonium salts which may be used are ammonium phosphates such as $(NH_4)_2HPO_4$ or $(NH_4)H_2PO_4$.

The microorganisms are cultured in appropriate media prior to the actual biotransformation. Examples of appropriate culture media are the media described in Tables 3 and 5.

The cultivation is usually carried out at a temperature of from 20 to 40° C. and at a pH of between 5 and 8, preferably at a temperature of from 25 to 35° C. and at a pH of between 6 and 7.5.

Expediently, the active enzymes, i.e. nitrile hydratases, are induced during cultivation by adding an enzyme inducer.

Enzyme inducers which may be used are saturated or unsaturated aliphatic nitriles or the corresponding amides. Aliphatic nitriles which may be used are all $C_{2-7}$-alkanenitriles, such as, for example, butyronitrile, isobutyronitrile, valeronitrile or isovaleronitrile, or $C_{3-7}$-alkenenitriles, such as, for example, methacrylonitrile or crotononitrile. Aliphatic amides which may be used are any $C_{2-7}$-alkanamides, such as, for example, butyramide, isobutyramide, valeramide or propionamide, or $C_{3-7}$-alkenamides, such as, for example methacrylamide or crotonamide. Preferred enzyme inducers are methacrylamide, butyramide, isobutyramide, valeramide, methacrylonitrile, crotonamide, butyronitrile and isobutyronitrile. Particular preference is given to using methacrylonitrile as enzyme inductor.

The microorganisms of the invention tolerate an acetonitrile concentration of at least 3 M, meaning that the enzyme activity is stable after incubation with 3 M acetonitrile in 0.1 M potassium phosphate buffer at pH 7.0 and 20° C. for 1 hour, i.e. that no more than 10% of activity is lost. Preferred microorganisms tolerate an acetonitrile concentration of at least 6 M for 1 hour under the abovementioned conditions, with a loss of activity of no more than 50%. Particularly preferred microorganisms tolerate an acetonitrile concentration of at least 9 M for 1 hour under the conditions mentioned, with a loss of activity of no more than 70%.

In very particularly preferred microorganisms, the enzyme activity is stable even after several minutes of incubation with 15 M and 19 M acetonitrile (corresponding to pure acetonitrile). Thus the loss of enzyme activity after 10 minutes of incubation with 15 M acetonitrile is less than 10%.

The microorganisms of the invention have high thermal stability, i.e. higher stability at high temperatures than the microorganisms known to date. The loss of enzyme activity of the microorganisms of the invention is preferably no more than 10% after incubation in 0.1 M potassium phosphate buffer, pH 7.0 at 60° C. for 1 hour, and the loss of enzyme activity after incubation under the conditions mentioned for 2 hours is no more than 40%.

Enzyme activity here means nitrile hydratase activity, in particular nitrile hydratase activity with respect to the substrate 3-cyanopyridine.

Further properties of the microorganisms of the invention are a high tolerance with respect to the preferably employed substrate 3-cyanopyridine and with respect to the product nicotinamide produced therefrom and a lower $K_M$ value with respect to 3-cyanopyridine. Another particularly outstanding property is the fact that they can accumulate acetamide at a higher concentration than that corresponding to the concentration of an acetamide solution saturated at 30° C. (approx. 220-230 g of acetamide in 100 ml of water).

Preferred microorganisms belong to the genus *Rhodococcus*. Particularly preferred microorganisms are the strain *Rhodococcus* sp. FZ4 and the functionally equivalent variants and mutants thereof. Functionally equivalent variants and mutants mean those variants and mutants which tolerate acetonitrile concentrations of at least 3 M. Very particular preference is given to "pigment-negative" *Rhodococcus* strains, i.e. strains which lack the red color which may lead to discoloration of the desired product. Such strains can, where appropriate, be readily generated from pigment-producing microorganisms by mutagenesis by means of UV radiation or mutagenic chemicals.

The strain *Rhodococcus* sp. FZ4 was deposited with the Deutsche Sammlung von Mikroorganismen and Zellkulturen GmbH (DSMZ), Mascheroder Weg 1b, D-38124 Braunschweig with deposition number DSM 13597 on Jul. 11, 2000, in accordance with the Budapest Treaty. It was not possible to classify this microorganism on the basis of its identification data to any, of the previously known *Rhodococcus* species, and it was therefore classified as a novel species.

The functionally equivalent variants and mutants of the strain *Rhodococcus* sp. FZ4 can be produced either by spontaneous mutation or, for example, by UV irradiation or mutagenic chemicals. Preferred variants and mutants of the *Rhodococcus* sp. FZ4 strain are "pigment-negative", i.e. they lack the red color which may lead to discoloration of the desired product.

The enzyme extract may be obtained, for example, by disrupting the microorganisms, for example by means of ultrasound, French press or by means of the lysozyme method.

The inventive enzymes having nitrile hydratase activity can be obtained from the above-described microorganisms. They are preferably obtainable from the microorganisms of the genus *Rhodococcus*, in particular from the microorganism *Rhodococcus* sp. FZ4 (DSM 13597).

Said enzymes have, in particular, the following properties:

a) a $K_M$ value of 2.84±1.00 mM for the substrate acetonitrile and of 80.5±15.0 mM for the substrate 3-cyanopyridine, in each case in 0.05 M potassium phosphate buffer, pH 7.0 at 25 20° C.;
b) a pH optimum of pH 6.5±1.0 at 20° C. in 0.05 M potassium phosphate buffer.

In particular, said enzymes have c) a native molecular weight of 465±50 kDa, determined by HPLC.

The actual biotransformation may be carried out using the above-described microorganisms, an enzyme extract of said microorganisms or the isolated enzyme. Preference is given to carrying out the biotransformation using the microorganism *Rhodococcus* sp. FZ4.

Substrates which may be used for the biotransformation are nitrites of the general Formula $R^1$—CN II.

In the general formula II, the substituent $R^1$ is a $C_{1-6}$-alkyl group, a $C_{2-6}$-alkenyl group or a group of the general formula IV

X

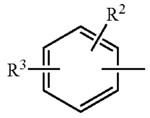

In the general formula IV, X is a nitrogen atom or —CH═, and the substituents $R^2$ and $R^3$ are, independently of one another, a hydrogen atom, a halogen atom, a $C_{1-6}$-alkyl group or a $C_{2-6}$-alkenyl group.

$C_{1-6}$-alkyl groups which may be used are methyl, ethyl, propyl, isopropyl, butyl, tert-butyl, isobutyl, pentyl and its isomers, and hexyl and its isomers. Examples of $C_{2-6}$-alkenyl groups which may be used are vinyl, allyl, 1-propen-1-yl and 1-propen-2-yl.

Halogen atoms which may be used are F, Cl , Br or I.

Preferred representatives of the nitriles of the general formula II are acetonitrile, butyronitrile, acrylonitrile, propionitrile, crotononitrile, 2-cyanopyridine, 3-cyanopyridine, 4-cyanopyridine, benzonitrile, fluorobenzonitrile, chlorobenzonitrile and bromobenzonitrile. The most preferred substrates are acetonitrile and 3-cyanopyridine.

The biotransfornation is preferably carried out with a single or continuous addition of substrate. As is known to the skilled worker, the substrate concentration to be used depends on the solubility of the substrate to be used.

Preference is given to carrying out the method using resting (non-growing) cells.

Media which may be used for the biotransformation are those known in the art, for example low-molarity phosphate buffers, HEPES buffer, citrate buffer and borate buffer. Low-molarity phosphate buffer means preferably a 0.01 to 0.5 M phosphate buffer, particularly preferably a 0.05 to 0.25 M phosphate buffer.

Preference is given to carrying out the biotransformation at a temperature of from 5 to 50° C., particularly preferably at a temperature of from 20 to 40° C. The preferred pH is between 5 and 10, the particularly preferred between 6 and 7.5.

After converting the nitrile of the general formula II, it is then possible to isolate the corresponding amides of the general formulae $R^1$—$CONH_2$ III, in which $R^1$ is defined as mentioned above, where appropriate after removing the cells, by using common work-up methods such as, for example, crystallization or spray drying.

The present invention furthermore relates to the use of the above-described microorganisms, in particular of the genus *Rhodococcus*, for removing acetonitrile waste.

Acetonitrile is a solvent which is used, for example, in HPLC and which, ultimately, needs to be disposed of as waste. For the inventive removal of acetonitrile waste, acetonitrile may be present at a concentration of up to a maximum of 19 M, corresponding to pure acetonitrile. Advantageously, a solution or suspension of from 0.25 to 15.0 M, preferably from 1 to 10 M, acetonitrile is used.

To remove acetonitrile waste, the microorganisms are advantageously used at a temperature of from 5 to 50° C., preferably at a temperature of from 20 to 40° C. The pH is advantageously between 5 and 10, preferably between 6 and 8.

The duration of the conversion of acetonitrile to acetamide for removing waste depends on the acetonitrile concentration and is, for example, approx. 2 hours for producing a 9.5 M acetamide solution/suspension at pH 7.0 and a temperature of approx. 20° C.

Identification of strain FZ4 (DSM 13597):

A) Chemotaxonomic markers:

1. diagnostic amino acid of peptidoglycan: mesodiaminopimelic acid
2. mycolic acids: mycolic.acids having a chain length of from $C_{40}$ to $C_{48}$ are present
3. fatty acid patterns: linear, saturated and unsaturated fatty acids and a high proportion of tuberculostearic acid are present. On the basis of the fatty acid patterns, strain FZ4 was identified as a member of the genus *Rhodococcus*.

B) Conventional markers:

The macroscopic appearance and morphology of the cells of strain FZ4 were similar to *Rhodococcus rhodochrous*. The colonies of strain FZ4 are salmon-red (RAL 3022), and young cultures developed branched hyphae which developed into rods and cocci.

Owing to the chemotaxonomic and conventional markers, strain FZ4 was identified as belonging to the species *Rhodococcus rhodochrous*, but having a low correlation factor.

C) Analysis of the first 500 bases of the 16s rDNA:

The sequence of the first 500 bases of the 16S rDNA reveals a similarity of only 97.7% to that of the typical representative strain of the species *Rhodococcus rhodochrous, Rhodococcus rhodochrous* DSM 43241 and of 99.1% to another *Rhodococcus rhodochrous* reference strain. Since the similarity of the sequence of the first 500 bases of the 16S rDNA of strain FZ4 to that of strain *Rhodococcus rhodochrous* DSM 43241 was below 99.5%, it was not possible to identify strain FZ4 as a member of the species *Rhodococcus rhodochrous*.

Strain FZ4 was therefore identified as a novel species within the genus *Rhodococcus*.

DESCRIPTION OF DRAWINGS

FIG. 2 depicts the temperature optimum of the *Rhodococcus* sp. FZ4 nitrile hydratase activity in resting cells.

FIG. 3 depicts the thermal stability of *Rhodococcus* sp. FZ4 nitrile hydratase activity in resting cells.

FIG. 4 depicts the pH optimum of *Rhodococcus* sp. FZ4 nitrile hydratase activity in resting cells.

FIG. 5 depicts the pH stability of *Rhodococcus* sp. FZ4 nitrile hydratase activity in resting cells.

FIG. 16 depicts the pH optimum of purified *Rhodococcus* sp. FZ4 nitrile hydratase.

FIG. 17 depicts the pH stability of purified *Rhodococcus* sp. FZ4 nitrile hydratase.

EXAMPLE 1

Determination of Nitrile Hydratase Activity

Figure 1:
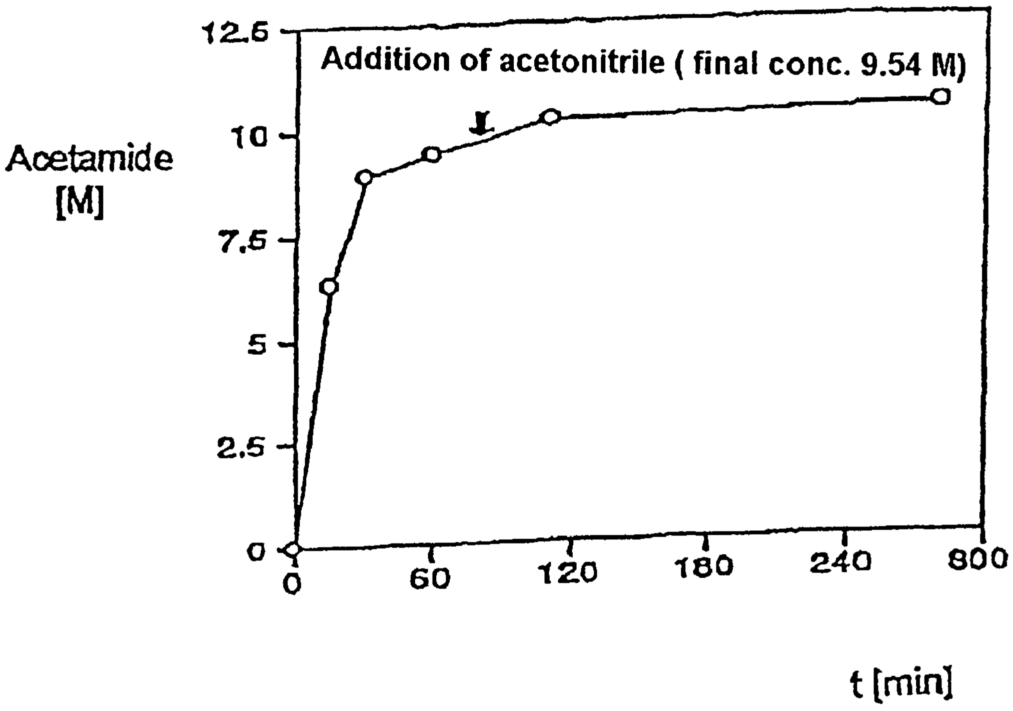
FIG. 1 depicts the biotransformation of acetonitrile to acetamide using resting cells of *Rhodococcus* sp. FZ4.

Nitrile hydratase activity was determined by incubating a reaction mixture comprising 3-cyanopyridine (1.0 M; 1.0 ml), potassium phosphate buffer (0.1 M, pH 7.0; 0.5 ml) and cell suspension (0.5 ml) with stirring at 20° C. for 5 min. The reaction was stopped by adding HCl (5 M; 0.1 ml). After filtration (0.2 μm filter) of the reaction mixture, the amount of nicotinamide produced was determined by means of HPLC (Waters Spherisorb 5 μ ODS2 (4.6×150 mm); $KH_2PO_4/H_3PO_4$ (10 mM; pH 2.8)/acetonitrile=9:1 (v/v); 1 ml/min; 230 nm). The total activity is expressed as μmol of nicotinamide produced/ (min×ml) and the specific activity is expressed as μmol of nicotinamide produced/(min×ml×$OD_{610\ nm}$).

EXAMPLE 2

Isolation of Strain *Rhodococcus* sp. FZ4 (DSM 13597)

Arch. Microbiol. 1998;170:85-90 describes strain *Rhodococcus* sp. YH3-3 (TPU 3453) metabolizing 3-pyridinaldoxime via 3-cyanopyridine and nicotinamide to nicotinic acid. In this case, aldoxime dehydratase activity and also nitrile hydratase activity and amidase activity of strain *Rhodococcus* sp. YH3-3 (TPU 3453) were induced by both various aldoximes and nitrites.

The enrichment medium of Table 1 was inoculated with various soil samples, followed by incubation at 37° C. for 7 to 10 days. The cultures thus obtained were transferred into the same medium and cultured again at 37° C. for another 7 to 10 days. This procedure was repeated three times. Subsequently, the cultures were diluted and plated out. After incubating the plates at 37° C. for 5 days, individual colonies were obtained. The individual colonies were assayed for the presence of a nitrile hydratase activity according to Example 1. In this way, strain *Rhodococcus* sp. FZ4 (DSM 13597) was isolated. It is also possible to use the nitrites acetonitrile, propionitrile, butyronitrile, crotononitrile, adiponitrile and malononitrile as carbon sources instead of 3-pyridinaldoxime.

TABLE 1

Enrichment medium

| Components | Concentration [g/l] |
|---|---|
| 3-pyridinaldoxime | 3.0 or 1.0 |
| $(NH_4)_2HP0_4$ | 2.0 |
| $KH_2PO_4$ | 2.0 |
| NaCl | 1.0 |
| $MgSO_4x7H20$ | 0.2 |
| $CoC1_2x6H_2O$ | 0.01 |
| Yeast extract | 0.2 |

to 1:1 with water (pH 7.0)

EXAMPLE 3

Influence of Cofactors on *Rhodococcus* sp. FZ4 Nitrile Hydratase Activity During Cultivation The preculture medium of Table 2 was inoculated with strain *Rhodococcus* sp. FZ4 (DSM 13597), followed by incubation with shaking at 28° C. for 1 to 2 days. The preculture was transferred into the basal medium of Table 3, which contains either $CoCl_2$ or $FeSO_4$, and cultured with shaking at 28° C. for 2 to 3 days. Nitrile hydratase activity was determined according to Example 1. The results are summarized in Table 4. A nitrile hydratase activity was present only when culturing *Rhodococcus* sp. FZ4 in the presence of cobalt.

TABLE 2

Preculture medium

| Components | Concentration [g/l] |
|---|---|
| Peptone | 5.0 |
| Meat extract | 5.0 |
| NaCl | 2.0 |
| Yeast extract | 0.5 |

to 1:1 with water (pH 7.0)

TABLE 3

Basal medium

| Components | Concentration [g/l] |
|---|---|
| Yeast extract | 2.0 |
| Peptone | 0.2 |
| L-glutamate, sodium salt | 15.0 |
| $MgSO_4x7H_2O$ | 0.5 |
| $CoC1_2x6H_2O$ (or $FeSO_4x7H_2O$) | 0.004 |
| Crotonamide | 5.0 |

to 1:1 with water (pH 6.8)

TABLE 4

Influence of cofactors on nitrile hydratase activity during cultivation

| Cofactor | Growth [$OD_{610\,nm}$] | Total activity [μmol/(min × ml) | Specific activity [μmol/(min × ml × $OD_{610\,nm}$)] |
|---|---|---|---|
| $FeSO_4$ | 2.86 | 0.989 | 0.346 |
| $CoC1_2$ | 2.79 | 38.1 | 13.1 |

EXAMPLE 4

Influence of Inducers on *Rhodococcus* sp. FZ4 Nitrile Hydratase Activity During Cultivation The preculture medium of Table 2 was inoculated with strain *Rhodococcus* sp. FZ4 (DSM 13597), followed by incubation with shaking at 28° C. for 1 to 2 days. The preculture was transferred into the culture medium of Table 5, which contained different inducers, and cultured with shaking at 28° C. for 3 days. Nitrile hydratase activity was determined according to Example 1. The results are summarized in Table 6. *Rhodococcus* sp. FZ4 nitrile hydratase was expressed during cultivation only in the presence of an inducer.

TABLE 5

Culture medium

| Components | Concentration [g/l] |
|---|---|
| Yeast extract | 1.0 |
| Sodium citrate | 10.0 |
| Malt extract | 15.0 |
| Inducer | 0.2% (w/v) |
| $KH_2PO_4$ | 2.0 |
| $MgSO_4x7H_2O$ | 0.5 |
| $CoC1_2x6H_2O$ | 0.015 |

to 1:1 with water (pH 7.0)

TABLE 6

Influence of inducers on nitrile hydratase activity

| Inducer | Growth [$OD_{610\,nm}$] | Total activity [μmol/(min × ml) | Specific activity [μmol/(min × ml × $OD_{610\,nm}$)] |
|---|---|---|---|
| Methacrylamide | 4.55 | 569 | 125 |
| Isobutyramide | 3.55 | 387 | 109 |
| Butyramide | 4.7 | 344 | 73.2 |
| Methacrylonitrile | 4.61 | 330 | 71.5 |
| Crotonamide | 9.32 | 558 | 59.9 |
| Butyronitrile | 5.26 | 307 | 58.4 |
| Valeramide | 5.61 | 322 | 57.5 |
| Isobutyronitrile | 5.24 | 273 | 52.1 |
| Crotononitrile | 8.24 | 407 | 49.4 |
| Propionamide | 5.17 | 149 | 28.7 |
| Valeronitrile | 3.70 | 120 | 32.4 |
| Isocaprononitrile | 4.72 | 134 | 28.5 |
| Isovaleronitrile | 3.22 | 74.7 | 23.2 |
| Capronitrile | 4.54 | 104 | 23.0 |
| Propionitrile | 4.72 | 95.8 | 20.3 |
| Acrylamide | 5.17 | 60.5 | 11.7 |
| 3-Pentenenitrile | 4.62 | 62 | 13.4 |
| ϵ-Caprolactam | 4.44 | 40.3 | 9.08 |
| Benzonitrile | 5.62 | 40.3 | 7.17 |
| Picolinamide | 3.80 | 26.1 | 6.87 |
| — | 4.2 | 27.7 | 6.59 |
| Cyanoacetamide | 4.75 | 30.9 | 6.50 |
| Acetamide | 4.37 | 21.6 | 4.98 |
| Acetonitrile | 4.46 | 18.4 | 4.13 |

TABLE 6-continued

| Influence of inducers on nitrile hydratase activity | | | |
|---|---|---|---|
| Inducer | Growth $[OD_{610\,nm}]$ | Total activity [μmol/(min × ml)] | Specific activity [μmol/(min × ml × $OD_{610\,nm}$)] |
| 3-Cyanopyridine | 5.54 | 12.3 | 2.21 |
| Isonicotinamide | 5.03 | 10.9 | 2.17 |
| Benzamide | 3.88 | 8.24 | 2.12 |
| Acrylonitrile | 3.27 | 5:91 | 1.81 |
| Nicotinamide | 3.55 | 4.94 | 1.39 |
| Urea | 6.16 | 5.66 | 0.918 |

EXAMPLE 5

Cultivation of *Rhodococcus* sp. FZ4

The preculture medium of Table 2 was inoculated with strain *Rhodococcus* sp. FZ4, followed by incubation with shaking at 28° C. for 1 to 2 days. The preculture was transferred into the culture medium of Table 5, containing 6 g/l methacrylamide as inducer, and cultured with shaking at 28° C. for 3 days. After 48 h, additional methacrylamide (0.20 (v/v)) was fed in.

In Examples 6 to 13, resting *Rhodococcus* sp. FZ4 cells were used.

EXAMPLE 6

Substrate Specificity of *Rhodococcus* sp. FZ4 Nitrile Hydratase Activity

*Rhodococcus* sp. FZ4 nitrile hydratase activity with respect to different substrates was determined according to Example 1, except that the appropriate substrate was used instead of 3-cyanopyridine and that the HPLC conditions were modified according to the substrate used. Table 7 summarizes the substrate specificity of *Rhodococcus* sp. FZ4 nitrile hydratase activity in comparison with the substrate specificity of *Rhodococcus rhodochrous* J1 nitrile hydratase activity.

TABLE 7

| Comparison of substrate specificities of *Rhodococcus* sp. FZ4 and *Rhodococcus rhodochrous* J1 nitrile hydratase activities | | |
|---|---|---|
| Substrate | *Rhodococcus* sp. FZ4 Relative activity [%] | *Rhodococcus rhodochrous* J1 Relative activity [%] |
| Acetonitrile | 646 | 0 (nitrile hydratase A)<br>115 (nitrile hydratase B) |
| Acrylonitrile | 498 | 478 |
| Butyronitrile | 466 | 26 |
| Propionitrile | 412 | 435 |
| 3-Cyanopyridine | 100 | 100 |
| 4-Cyanopyridine | 98.4 | 70 |
| Crotononitrile | 92.1 | 78 |
| Benzonitrile | 41.7 | 27 |
| 2-Cyanopyridine | 39.3 | 45 |
| m-Chlorobenzonitrile | 39.3 | 43 |
| p-Chlorobenzonitrile | 8.25 | 13 |
| Methacrylonitrile | 3.64 | 87 |
| o-Chlorobenzonitrile | 0 | 2.8 |

EXAMPLE 7

Temperature Optimum and Thermal Stability of *Rhodococcus* sp. FZ4 Nitrile Hydratase Activity Nitrile hydratase activity was determined according to Example 1 at different temperatures in the range from 20 to 70° C. The temperature optimum for nitrile hydratase activity was at 60° C. (FIG. 2).

In order to determine the thermal stability of nitrile hydratase activity, the cell suspension was incubated at different temperatures in the range from 40 to 70° C. for 15 min. Nitrile hydratase activity was then determined at 20° C. according to Example 1. Nitrile hydratase activity after 15 minutes of incubation at temperatures in the range from 40 to 60° C. corresponded to the original nitrile hydratase activity (FIG. 3).

EXAMPLE 8 pH Optimum and pH Stability of *Rhodococcus* sp. FZ4 Nitrile Hydratase Activity

Nitrile hydratase activity was determined according to Example 1 using different buffers (0.1 M) at different pH values in the range from 3 to 12. The pH optimum of nitrile hydratase activity was between 6 and 7 (FIG. 4) .

In order to determine the pH stability of nitrile hydratase activity, the cell suspension was incubated at different pH values in the range from 4 to 10 at 20° C. for 24 h. The cell suspension was subsequently centrifuged and the removed cells were washed and resuspended in potassium phosphate buffer (0.1 M; pH 7.0). Nitrile hydratase activity was determined according to Example 1 and, after incubation at pH values in the range from 5 to 10 for 24 hours, corresponded approximately to the original nitrile hydratase activity (FIG. 5).

EXAMPLE 9

Figure 6:
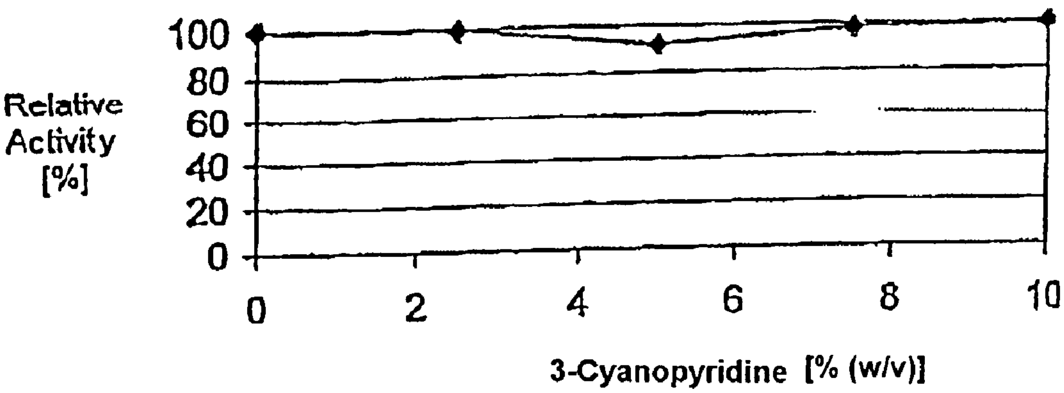
FIG. 6 depicts 3-cyanopyridine tolerance of *Rhodococcus* sp. FZ4 nitrile hydratase activity in resting cells.

Influence of 3-cyanopyridine Concentration on *Rhodococcus* sp. FZ4 Nitrile Hydratase Activity A cell suspension was incubated at different 3-cyano-30 pyridine concentrations in the range from 0 to 10% (w/v) at 20° C. for 60 min. The cells were removed, washed and resuspended in potassium phosphate buffer (0.1 M; pH 7.0). Nitrile hydratase activity was determined according to Example 1 and, after incubation at 3-cyanopyridine concentrations in the range from 0 to 20% (w/v) for 60 minutes, corresponded approximately to the original nitrile hydratase activity (FIG. 6).

EXAMPLE 10

Figure 7:
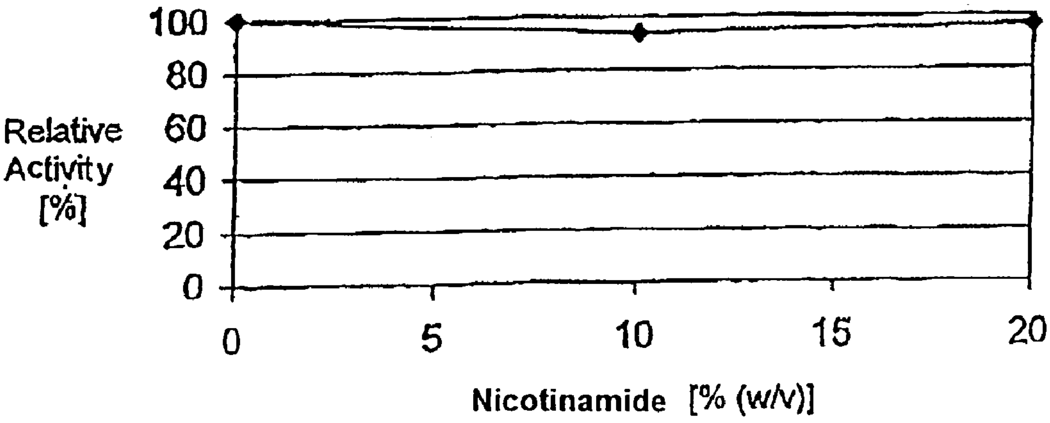
FIG. 7 depicts nicotinamide tolerance of *Rhodococcus* sp. FZ4 nitrile hydratase activity in resting cells.

Influence of Nicotinamide Concentration on *Rhodococcus* sp. FZ4 Nitrile Hydratase Activity A cell suspension was incubated at different nicotinamide concentrations in the range from 0 to 20% (w/v) at 20° C. for 24 h. The cells were removed, washed and resuspended in potassium phosphate buffer (0.1 M; pH 7.0). Nitrile hydratase activity was determined according to Example 1 and, after incubation at nicotinamide concentrations in the range from 0 to 20% (w/v) for 24 h, corresponded approximately to the original nitrile hydratase activity (FIG. 7).

EXAMPLE 11

Figure 10:
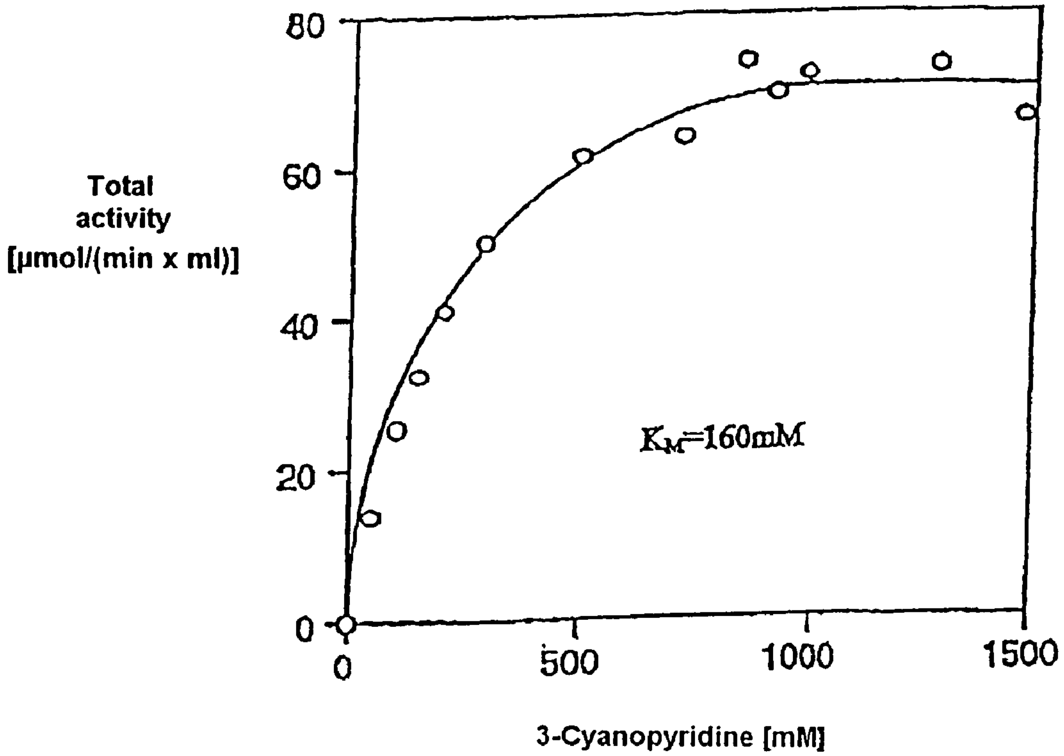
FIG. 10 depicts the *Rhodococcus* sp. FZ4 nitrile 5 hydratase activity in resting cells as a function of 3-cyanopyridine concentration.

Determination of the Km Value for 3-cyanopyridine with Respect to *Rhodococcus* sp. FZ4 Nitrile Hydratase A reaction mixture comprising 3-cyanopyridine 20 (0.1-1.0 M; 1.0-1.8 ml), aqueous NaCl solution (0.85% (w/v); 0.7 to 0.1 ml), potassium phosphate buffer (0.1 M; pH 7.0; 0.3 ml) and cell suspension (0.01 ml) was incubated with shaking at 30° C. for 10 min. The total volume of the reaction mixture was between 2.0 to 2.2 ml, depending on the 3-cyanopyridine concentration. The reaction was stopped by adding HC1(2 M; 0.1 ml). After centrifugation of the reaction mixture (12 000 rpm; 5 min), the amount of nicotinamide produced was determined by means of HPLC according to Example 1. The $K_M$ value determined was 160 mM (FIG. 10).

EXAMPLE 12

Comparison of *Rhodococcus* sp. FZ4 Nitrile Hydratase Activities with the Nitrile Hydratase Activities of the known Microorganisms *Amycolatopsis* sp. NA40, *Rhodococcus* sp. GF270 and *Rhodococcus rhodochrous* J1

The $K_M$ values for the substrate 3-cyanopyridine with respect to the nitrile hydratase activities of *Rhodococcus* sp. FZ4, *Rhodococcus* sp. GF270 (DSM 12211; WO 99/05306), *Amycolatopsis* sp. NA40 (DSM 11617; WO 99/05306) and *Rhodococcus rhodochrous* J1 were determined according to Example 11 using the respective microorganism.

The $K_M$ values of the strains *Amycolatopsis* sp. NA40 and *Rhodococcus* sp. FZ4 are lower than that of the other microorganisms (Table 8).

TABLE 8

Comparison of the $K_M$, values for the substrate 3-cyanopyridine

| $K_M$ [mM] | | | |
|---|---|---|---|
| *Rhodococcus* sp. FZ4 | *Rhodococcus* sp. GF270 | *Amycolatopsis* sp. NA40 | *Rhodococcus rhodochrous* J1 |
| 160 | >200 | 41.7 | 200 |

The thermal stability of the nitrile hydratase activities of *Rhodococcus* sp. FZ4, *Rhodococcus* sp. GF270, *Amycolatopsis* sp. NA40 and *Rhodococcus rhodochrous* J1 was determined according to Example 7 using the respective microorganism and the incubation conditions indicated in Table 9. The nitrile hydratase activity of the *Rhodococcus* sp. FZ9 strain exhibited the highest thermal stability compared to the nitrile hydratase activity of the other microorganisms.

TABLE 9

Comparison of the thermal stability of nitrile hydratase activities

| Incubation conditions | Relative activity [%]<br>*Rhodococcus* sp. FZ4 | *Rhodococcus* sp. GF270 | *Amycolatopsis* sp. NA40 | *Rhodococcus rhodochrous* J1 |
|---|---|---|---|---|
| 15 min at | | | | |
| 50° C. | 100 | 100 | nd[a] | 100 |
| 60° C. | 93 | 95 | nd[a] | 80 |
| 70° C. | 2 | 5 | nd[a] | 0 |
| 60 min at | | | | |
| 20° C. | 100 | 100 | 100 | nd[a] |
| 30° C. | 100 | 100 | 95 | nd[a] |

TABLE 9-continued

Comparison of the thermal stability of nitrile hydratase activities

| Incubation conditions | Relative activity [%]<br>*Rhodococcus* sp. FZ4 | *Rhodococcus* sp. GF270 | *Amycolatopsis* sp. NA40 | *Rhodococcus rhodochrous* J1 |
|---|---|---|---|---|
| 40° C. | 100 | 100 | 80 | nd[a] |
| 50° C. | 100 | 100 | 32 | nd[a] |
| 60° C. | 100 | 89 | 0 | nd[a] |
| 70° C. | 6 | 0 | 0 | nd[a] |
| 60° C. for | | | | |
| 0 min | 100 | 100 | nd[a] | nd[a] |
| 30 min | 100 | 67–80 | nd[a] | nd[a] |
| 60 min | 92–100 | 52–68 | nd[a] | nd[a] |
| 120 min | 72–87 | 29–47 | nd[a] | nd[a] |

[a]not determined.

The influence of 3-cyanopyridine concentration on the nitrile hydratase activities of *Rhodococcus* sp. FZ4, *Rhodococcus* sp. GF270, *Amycolatopsis* sp. NA40 and *Rhodococcus rhodochrous* J1 was determined according to Example 9 using the respective microorganism and the 3-cyanopyridine concentrations indicated in Table 10. The nitrile hydratase activities of the strains *Rhodococcus* sp. FZ4 and *Rhodococcus* sp. GF270 exhibit the highest tolerance of 3-cyanopyridine.

TABLE 10

Comparison of the influence of 3-cyano-pyridine concentration on nitrile hydratase activity

| 3-Cyano-pyridine [% (w/v)] | Relative activity [%]<br>*Rhodococcus* sp. FZ4 | *Rhodococcus* sp. GF270 | *Amycolatopsis* sp. NA40 | *Rhodococcus rhodochrous* J1 |
|---|---|---|---|---|
| 0 | 100[a] | 100[a] | 100[b] | 100[b] |
| 2.5 | 100[a] | 100[a] | 74[b] | nd[c] |
| 5.0 | 100[a] | 100[a] | 56[b] | 86[b] |
| 7.5 | 100[a] | 100[a] | 47[b] | nd[c] |
| 10.0 | 100[a] | 100[a] | 16[b] | 63[b] |

[a]Incubation for 60 min.
[b]incubation for 15 min.
[c]not determined

The influence of nicotinamide concentration on the nitrile hydratase activities of *Rhodococcus* sp. FZ4, *Rhodococcus* sp. GF270, *Amycolatopsis* sp. NA40 and *Rhodococcus rhodochrous* J1 was determined according to Example 9 using the respective microorganism and the nicotinamide concentration indicated in Table 11. The nitrile hydratase activities of the strains *Rhodococcus* sp. FZ4 and *Rhodococcus* sp. GF270 exhibit the highest tolerance of nicotinamide (Table 11).

TABLE 10

Comparison of the influence of nicotinamide concentration on nitrile hydratase activities

| *Nicotin amide* [% (w/v)] | Relative activity [%]<br>*Rhodococcus* sp. FZ4 | *Rhodococcus* sp. GF270 | *Amycolatopsis* sp. NA40 | *Rhodococcus rhodochrous* J1 |
|---|---|---|---|---|
| 0 | 100 | 100 | 100 | nd[a] |
| 10 | 100 | 100 | 55 | nd[a] |

TABLE 10-continued

| Comparison of the influence of nicotinamide concentration on nitrile hydratase activities Relative activity [%] | | | | |
|---|---|---|---|---|
| *Nicotin amide* [% (w/v)] | *Rhodococcus* sp. FZ4 | *Rhodococcus* sp. GF270 | *Amycolatopsis* sp. NA40 | *Rhodococcus rhodochrous* J1 |
| 20 | 100 | 100 | 0 | nd[a] |
| 30 | 100 | 100 | 0 | nd[a] |

[a]not determined

EXAMPLE 13

Biotransformation of 3-cyanopyridine to Nicotinamide Using *Rhodococcus* sp. FZ4

A solution of 3-cyanopyridine was added in 42 portions (42×0.52 g=21.8 g; 0.21 mol) to a charge comprising cell suspension (13.7 mg dry cell weight, 4 ml) and potassium phosphate buffer (0.1 M; pH 6.0; 16 ml). The next portion of 3-cyanopyridine was added to the reaction mixture, after the 3-cyanopyridine in the reaction mixture had been converted quantitatively to nicotinamide. The reaction mixture became solid during the course of the reaction. A total of 25.7 g (quantitative yield) of nicotinamide was produced.

EXAMPLE 14

Biotransformation of Acetonitrile to Acetamide Using *Rhodococcus* sp. FZ4

Acetonitrile (5 ml; 95 mmol) was added dropwise to a reaction mixture comprising potassium phosphate buffer (0.1 M; pH 7.0; 4.5 ml) and cell suspension (4.88 mg dry cell weight; 0.5 ml) at 20° C. over 80 min. The afterreaction was carried out with shaking at 20° C. Acetamide production during the reaction was monitored by means of HPLC (Waters Spherisorb 5μ ODS2 (4.6×150 mm); $KH_2PO_4$(10 mM; pH 2.5)/acetonitrile=99/1(v/v); 1.0 ml/min; 210 nm). 6.14 g (quantitative yield) of acetamide which accumulated in the reaction medium was produced within 120 min (FIG. 1).

EXAMPLE 15

Figure 8:
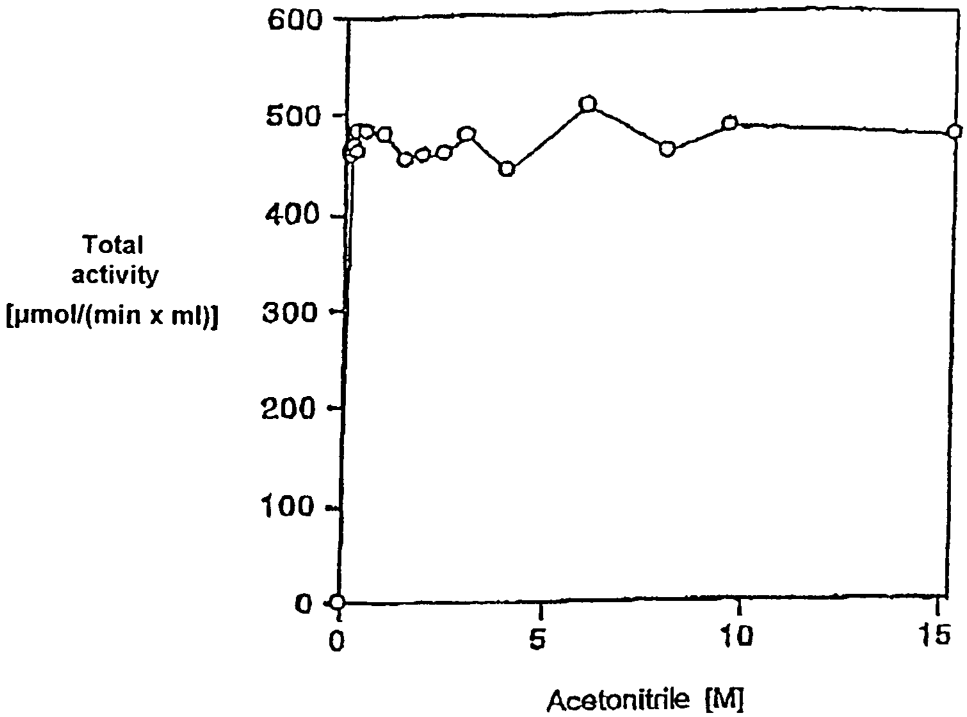
FIG. 8 depicts the influence of the acetonitrile concentration on *Rhodococcus* sp. FZ4 nitrile hydratase activity in resting cells in the biotransformation of acetonitrile to acetamide.

Influence of Acetonitrile Concentration on *Rhodococcus* sp. FZ4 Nitrile Hydratase Activity in the Biotransformation of Acetonitrile to Acetamide A reaction mixture comprising acetonitrile (0.2-19.0 M; 1.0-1.6 ml), aqueous NaCl solution (0.85% (w/v); 0.6-0.0 ml), potassium phosphate buffer (0.1 M; pH 7.0; 0.3 ml) and cell suspension (0.1 ml) was incubated with shaking at 20° C. for 10 min. The total reaction volume was 2.0 ml. The reaction was stopped by adding MeOH. The reaction mixture was centrifuged (12 000 rpm, 5 min) and the amount of acetamide produced was determined by means of HPLC according to Example 14. The nitrile hydratase activity was nearly constant in the range from 0.1 to 15 M acetonitrile (FIG. 8).

EXAMPLE 16

Influence of Acetonitrile Concentration on *Rhodococcus* sp. FZ4 Nitrile Hydratase Activity Cells were incubated with acetonitrile (0.0-15.0 M) in potassium phosphate buffer (0.1 M, pH 7.0) at 20° C. over 1 h. The cell suspension was centrifuged (12 000 rpm, 5 min) and the cells were resuspended in aqueous NaCl solution (0.85% (w/v)). A reaction mixture comprising this cell suspension (0.1 ml), 3-cyanopyridin (0.5 M; 1.0 ml), aqueous NaCl solution (0.85% (w/v); 0.6 ml) and potassium phosphate buffer (0.1 M; pH 7.0; 0.3 ml) was incubated with shaking at 30° C. for 5 min. The reaction was stopped by adding MeOH. The reaction mixture was centrifuged (12 000 rpm, 5 min) and the amount of acetamide produced was determined by means of HPLC according to Example 14.

Figure 9:
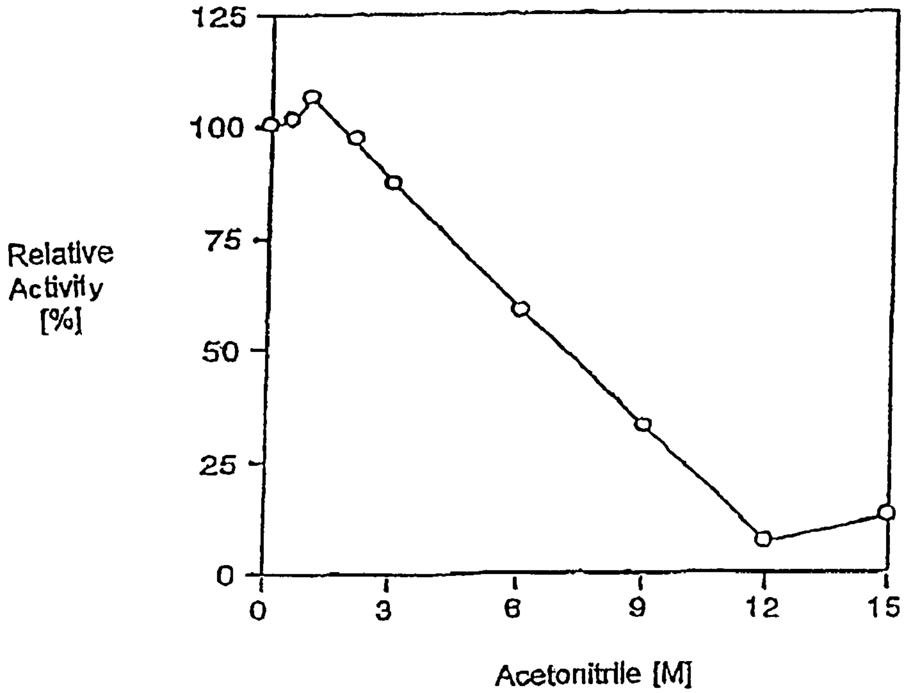
FIG. 9 depicts the influence of the acetonitrile concentration on *Rhodococcus* sp. FZ4 nitrile hydratase activity in resting cells.

The nitrile hydratase activity was nearly constant with acetonitrile in the concentration range from 0 to 3 M after 1 hour of incubation. After 1 hour of incubation with 6 M acetonitrile, 60% of the original nitrile hydratase activity was still present. After 1 hour of incubation with 9 M acetonitrile, approx. 35% of the original nitrile hydratase activity was still present (FIG. 9).

EXAMPLE 17

Generation of Pigment-negative *Rhodococcus* sp. FZ4 Mutants

"Nutrient broth" medium (50 ml) was inoculated with strain *Rhodococcus* sp. FZ4, followed by incubation with shaking at 28° C., until an $OD_{610\ nm}$ of 6.29 was reached. The preculture (10 ml) was then transferred to "nutrient broth" medium (25 ml) and incubated with shaking at 28° C., until an $OD_{610\ nm}$, of 1.90 was reached. The culture (10 ml) thus obtained was centrifuged (8 000 rpm, 5 min). The supernatant was discarded and the cell precipitate was suspended in phosphate-buffered saline. The cell suspension was centrifuged (8 000 rpm, 5 min). The supernatant was discarded and the cell precipitate was suspended in phosphate-buffered saline (5 ml). The cell suspension was transferred to a glass petri dish (90 mm diameter). The cells were irradiated using a UV lamp (15 W, 254 nm) from a distance of 25 cm for 17 min. The cells were then incubated with shaking in double-concentrated "nutrient broth" medium at 28° C. for 4 days. The culture thus obtained was diluted 100 times, and 100 μ 1 aliquots thereof were plated out on "plate count agar" and incubated at 28° C. Almost 150 single colonies grew per plate. The plates were exposed to daylight, in order to induce the formation of red pigments. The colonies of pigment-negative mutants were readily distinguishable from those of the colored mutants and those of the red wild type.

EXAMPLE 18

Purification of *Rhodococcus* sp. FZ4 Nitrile Hydratase

*Rhodococcus* sp. FZ4 was cultured according to Example 3 in a 2-1 fermenter. The culture was centrifuged and the cell precipitate resuspended in aqueous NaCl solution (0.85% (w/v)). The cell suspension was transferred to potassium phosphate buffer (0.1 M; pH 7.0) containing butyric acid (44 mM) and sonicated. Cell debris was removed by centrifugation. The supernatant was used for the purification of nitrile hydratase according to Table 12. Nitrile hydratase activity was determined according to Example 1, using, however, the respective extracts instead of the cell suspension.

TABLE 12

| Purification of *Rhodococcus* sp. FZ4 nitrile 5 hydratase | | | |
|---|---|---|---|
| Purification step | Protein content [mg] | Total activity [μmol/min] | Specific activity [μmol/(min × mg)] |
| Cell-free extract | 335 | 5 881 | 17.6 |
| $(NH_4)_2SO_4$ precipitation | 198 | 6 087 | 28.4 |
| DEAF-Sephacel | 73.0 | 3 553 | 48.7 |
| Butyl-Toyopearl | 66.2 | 2 035 | 30.7 |
| Phenyl-Sepharose | 26.2 | 890 | 34.0 |

EXAMPLE 19

Molecular Weight Determination of Purified Nitrile Hydratase

The molecular weight was determined by means of HPLC (TSK gel G 300 SW (0.75×60 cm); potassium phosphate buffer (0.1 M; pH 7.5) and potassium chloride (0.2 M); 0.7 ml/min; 280 nm).

Figure 11:
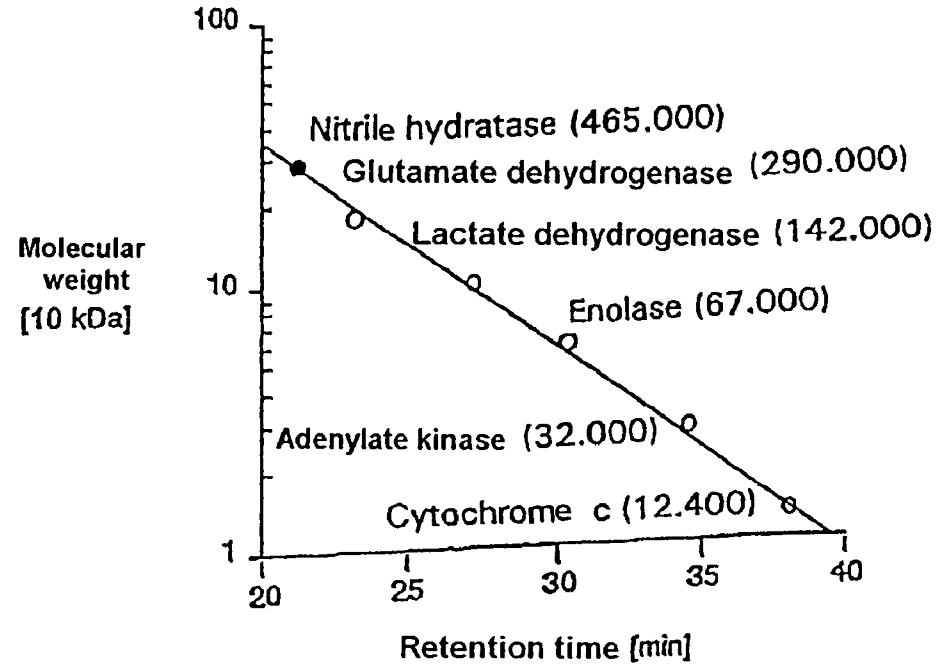
FIG. 11 depicts the logarithmic plot of the molecular weights of nitrile hydratase and of reference proteins as a function of the respective HPLC retention time.

The molecular weight of nitrile hydratase was 465 kDa (FIG. 11).

Figure 12:
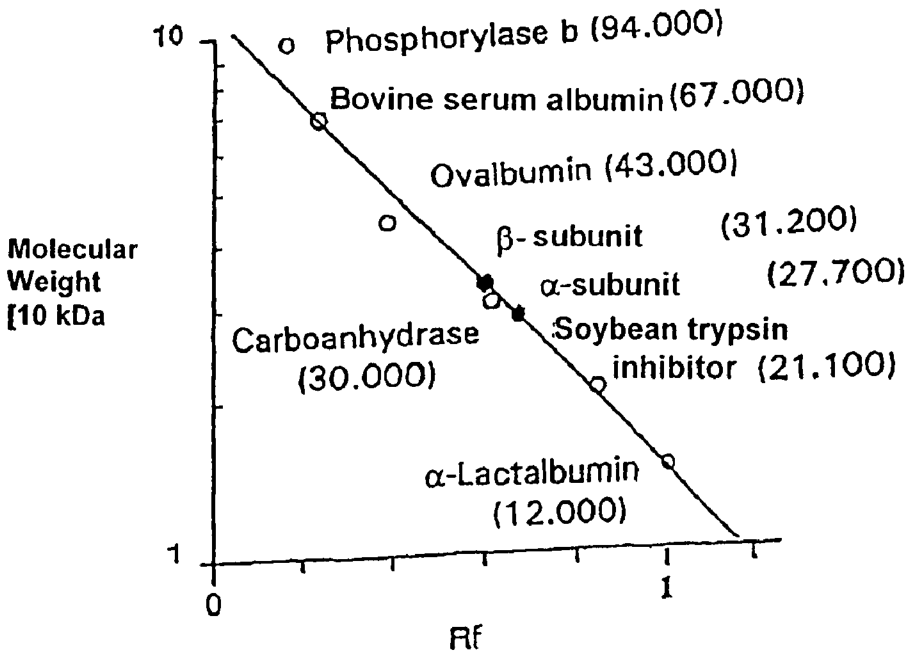
FIG. 12 depicts the logarithmic plot of the molecular weights of nitrile hydratase subunits and of reference proteins as a function of the respective SDA Page RF value.

Nitrile hydratase consists of an α-subunit having a molecular weight of 27.7 kDa and a β-subunit having a molecular weight of 31.2 kDa (FIG. 12).

EXAMPLE 20

Thermal Stability of Purified Nitrile Hydratase

Figure 15:
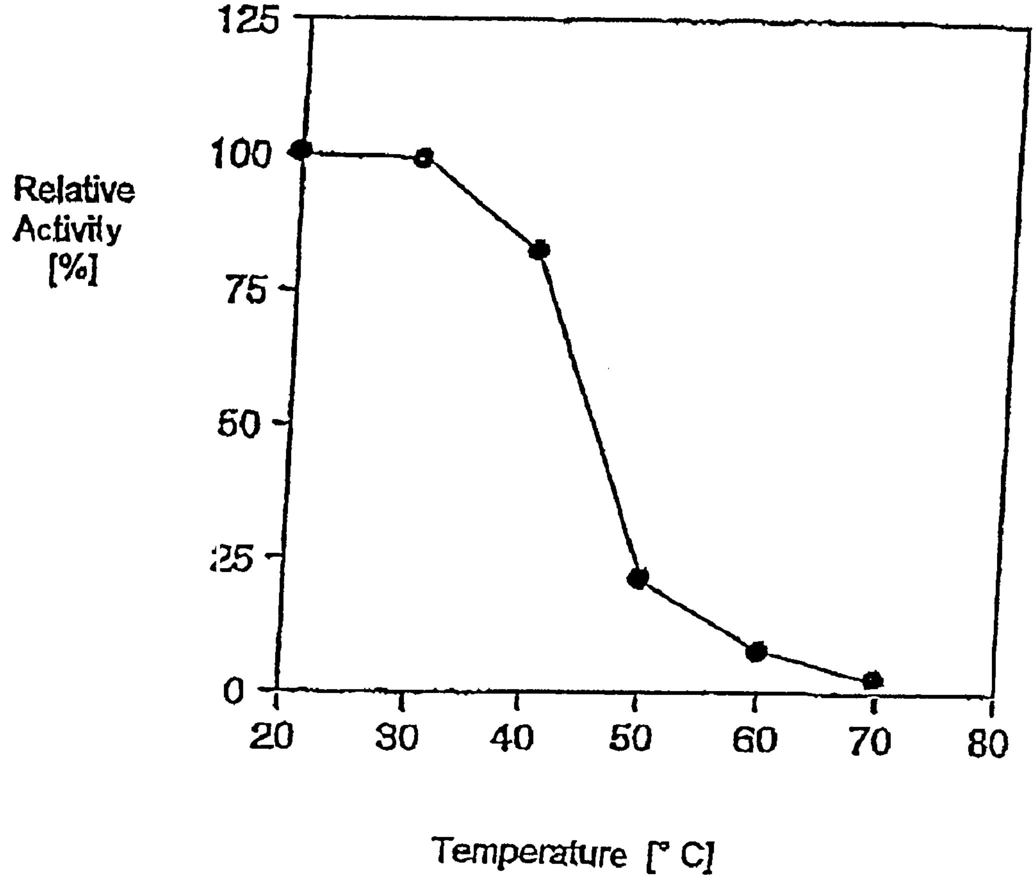
FIG. 15 depicts the thermal stability of purified *Rhodococcus* sp. FZ4 nitrile hydratase.

A solution comprising nitrile hydratase solution 25 (0.697 μmol/min; 0.025 ml) and potassium phosphate buffer (0.1 M; pH 7.0; 0.475 ml) was incubated at different temperatures in the range from 20 to 70° C. for 60 min. The solution was then cooled to 20° C. using an ice bath and 3-cyanopyridine (0.5 M; 0.500 ml) was 30 added. The reaction mixture was incubated at 20° C. for 10 min. The reaction was stopped by adding MeOH. The amount of nicotinamide produced was determined by means of HPLC according to Example 1. After 60 minutes of incubation at temperatures above 40° C., nitrile hydratase activity decreased markedly and, after 60 min of incubation at 50° C., nitrile hydratase activity was only about 25% of the original activity (FIG. 15).

EXAMPLE 21 pH Optimum of Purified Nitrile Hydratase

A reaction mixture comprising 3-cyanopyridine (0.5 M; 0.500 ml), nitrile hydratase solution (0.697 μmol/min; 0.025 ml) and different buffers in the pH range from 4 to 11 (0.1 M; 0.0475 ml) was incubated at 20° C. for 10 min. The reaction was stopped by adding MeOH. The amount of nicotinamide produced was determined by means of HPLC according to Example 1. The pH optimum of nitrile hydratase was in the range from 6.0 to 6.5 (FIG. 16).

EXAMPLE 22 pH Stability of Purified Nitrile Hydratase

A solution comprising nitrile hydratase solution (8.36 μmol/min; 0.47 ml), different buffers in the pH range from 4.0 to 11.0 (0.3 M; 0.10 ml) and distilled water (0.03 ml) was incubated at 20° C. for 30 min. A reaction mixture comprising an aliquot of the incubated nitrile hydratase solution (0.05 ml), 3-cyanopyridine (0.5 M; 0.5 ml) and the respective buffer (0.1 M; 0.45 ml) was incubated at 20° C. for 10 min. The reaction was stopped by adding MeOH. The amount of nicotinamide produced was determined by means of HPLC according to Example 1. After 60 minutes of incubation at a pH in the range from 6 to 8, nitrile hydratase activity corresponded approximately to the original nitrile hydratase activity (FIG. 17).

EXAMPLE 23

Substrate-specificity of Purified Nitrile Hydratase

A reaction mixture comprising nitrile hydratase solution (0.695 μmol/min; 0.025 ml), different substrates (0.500 ml) and potassium phosphate buffer (0.1 M; pH 7.0; 0.475 ml) was incubated at 20° C. for 5 to 10 min. The concentrations of the substrates used were in the range from 0.015 to 0.250 M. The reaction was stopped by adding MeOH. The amount of amide produced was determined by means of HPLC. The results are summarized in Table 13. With the substrates assayed, nitrile hydratase activity is highest with respect to the substrate acetonitrile.

TABLE 13

| Substrate specificity of purified nitrile hydratase | | |
|---|---|---|
| Substrate | Concentration [M] | Relative activity [%] |
| Acetonitrile | 0.2 | 1 008 |
| Acrylonitrlie | 0.2 | 774 |
| Propionitrile | 0.2 | 693 |
| Butyronitrile | 0.2 | 578 |
| Crotononitrile | 0.2 | 114 |
| 3-Cyanopyridine | 0.25 | 100[a] |
| 4-Cyanopyridine | 0.125 | 92.8 |
| Benzonitrile | 0.015 | 75.6 |
| m-Chlorobenzonitrile | 0.015 | 66.5 |
| 2-Cyanopyridine | 0.125 | 36.7 |
| p-Chlorobenzonitrile | 0.015 | 8.31 |
| Methacrylamide | 0.2 | 1.39 |
| o-Chlorobenzonitrile | 0.015 | 0 |

[a]Total activity: 4,164 μmol/(min × .ml).

EXAMPLE 24

Influence of Potential Inhibitors on Purified Nitrile Hydratase

A solution comprising nitrile hydratase solution (0.695 μmol/min; 0.025 ml), potassium phosphate buffer (0.1 M; pH 7.0; 0.475 ml), distilled water (0.150 ml) and different potential inhibitors (0.100 ml) was incubated at 20° C. for 5 min. This was followed by the addition of 3-cyanopyridine (1.0 M; 0.250 ml). The concentration of the inhibitors in the reaction mixture was 1.0 mM. The reaction mixture was incubated at 20° C. for 10 min. The reaction was stopped by adding MeOH. The amount of nicotinamide produced was determined by means of HPLC according to Example 1. The results are summarized in Table 14. Among the potential inhibitors tested, hydroxylamine and potassium cyanide exhibit the strongest inhibitor action.

TABLE 14

| Influence of potential inhibitors on purified nitrile hydratase | |
|---|---|
| Potential inhibitor | Relative activity [%] |
| p-Chloromercuribenzoic acid[a] | 187 |
| Tiron | 114 |
| Phenylmethanesulfonyl fluoride | 110 |
| 1,10-Phenanthroline | 106 |
| Urea | 106 |
| Dithiothreitol | 103 |
| EDTA[b] | 100 |
| — | 100 |
| Cysteamine | 99.1 |
| 8-Hydroxyquinoline | 97.8 |
| 2,2'-Bipyridyl | 97.8 |
| Iodoacetate | 96.7 |
| N-Ethylmaleinimide | 95.3 |
| Sodium azide | 93.5 |
| 5,5'-Dithiobis(2-nitrobenzoic acid)[a] | 93.4 |
| Diethyldithiocarbamate | 93.3 |
| D-Cycloserine | 86.3 |
| Phenylhydrazine | 84.6 |
| 2-Mercaptoethanol | 76.3 |
| Hydroxylamine | 1.34 |
| Potassium cyanide | 0 |

[a]0.1 MM. b Ethylenediaminetetraacetic acid.
[b]total activity: 3,776 µmol/(min x ml)

EXAMPLE 25

Influence of Metal Ions on the Activity of Purified Nitrile Hydratase

The influence of metal ions on the activity of purified nitrile hydratase was carried out according to Example 24, but with the addition of metal ions instead of potential inhibitors. The concentration of the metal ions in the reaction mixture was 1.0 mM. The results 15 are summarized in Table 15. Of the metal ions assayed, only silver cations and divalent mercury cations exhibit inhibitor action.

TABLE 15

| Influence of metal ions on the activity of purified nitrile hydratase | |
|---|---|
| Metal ions | Relative activity [%] |
| $CuS0_4$ | 177 |
| $MnCl_2$ | 123 |
| $NiCl_2$ | 123 |
| $ZnSO_4$ | 121 |
| $FeSO_4$ | 113 |
| $CaCl_2$ | 113 |
| $CoCl_2$ | 110 |
| $FeCl_3$ | 105 |
| — | 100[a] |
| $AgNO_3$ | 0 |
| $HgCl_2$[b] | 0 |

[a]Total activity: 3,375 µmol/(min x ml).
[b]0.1 mM

EXAMPLE 26

Determination of the Km Value for 3-cyanopyridine with Respect to Purified Nitrile Hydratase 3-Cyanopyridine was added at different concentrations (3.1-800 mM; 0.500 ml) to a solution comprising nitrile hydratase solution (0.0697 µmol/min; 0.025 ml) and 15 potassium phosphate buffer (0.1 M; pH 7.0; 0.475 ml). The reaction mixture was incubated at 20° C. for 10 min. The reaction was stopped by adding methanol and the amount of nicotinamide produced was determined by means of HPLC according to Example 1.

Figure 13:
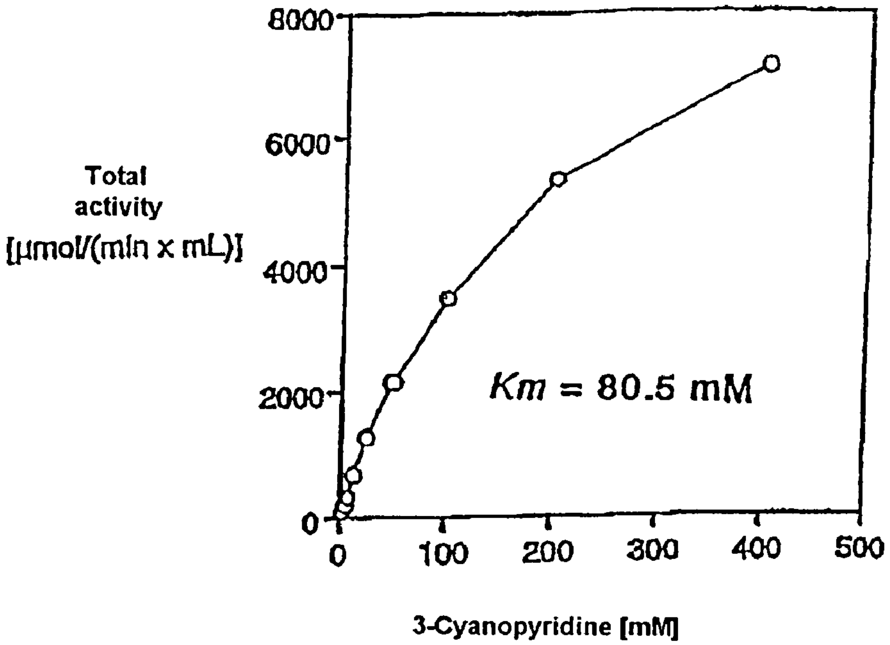
FIG. 13 depicts the activity of purified *Rhodococcus* sp. FZ4 nitrile hydratase as a function of the 3-cyanopyridine concentration.

The $K_M$ value for 3-cyanopyridine was 80.5 mM (FIG. 13).

EXAMPLE 27

Figure 14:
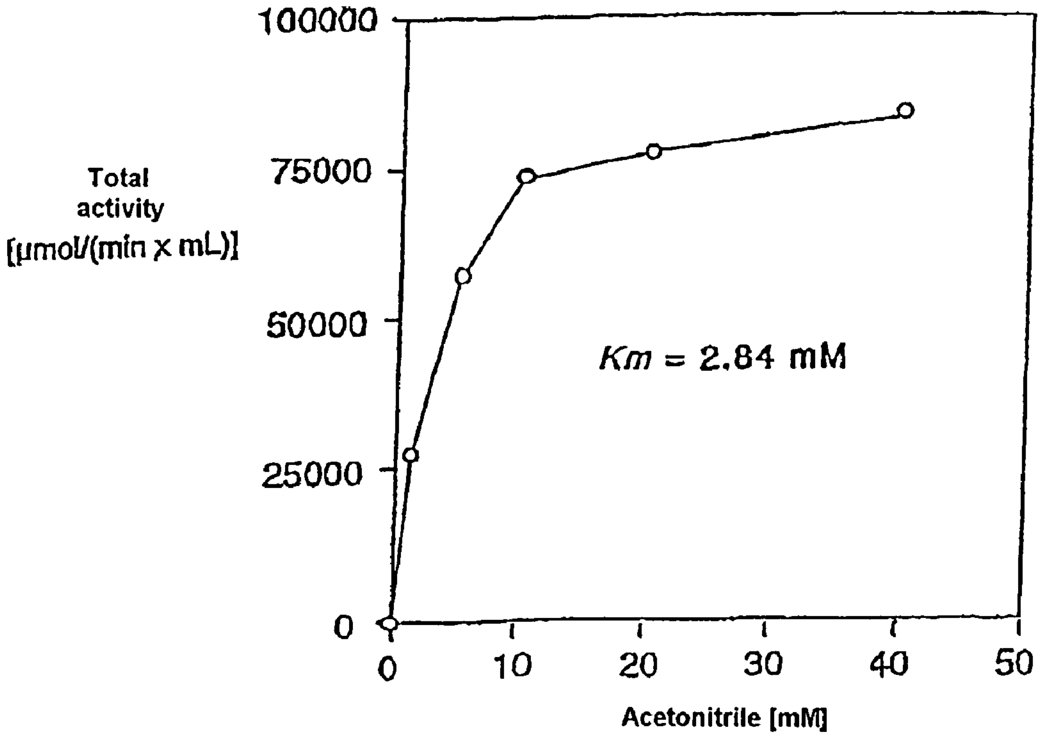
FIG. 14 depicts the activity of purified *Rhodococcus* sp. FZ4 nitrile hydratase as a function of acetonitrile concentration.

Determination of the $K_M$ Value for Acetonitrile with Respect to Purified Nitrile Hydratase Acetonitrile was added at different concentrations (2.5-80 mM; 0.500 ml) to a solution comprising nitrile hydratase solution (0.0697 µmol/min; 0.025 ml) and potassium phosphate buffer (0.1 M; pH 7.0; 0.475 ml). The reaction mixture was incubated at 20° C. for 10 min. The reaction was stopped by adding methanol and the amount of acetamide produced was determined by means of HPLC according to Example 14. The $K_M$ value for acetonitrile was 2.84 mM (FIG. 14).

Various publications are cited herein, the contents of which are hereby ated by reference in their entireties.

What is claimed is:

1. A method for preparing amides of the general formula $R^1$—$CONH_2$ III wherein $R^1$ is selected from the group consisting of a $C_{1-6}$-alkyl radical, a $C_{2-6}$-alkenyl group or a group of the general formula

IV

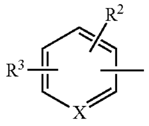

wherein X is a nitrogen atom or —CH═, wherein $R^2$ and $R^3$ are selected from the group consisting of a hydrogen atom, a halogen atom, a $C_{1-6}$-alkyl group or a $C_{2-6}$-alkenyl group, wherein said method a nitrile of the general formula $R^1$—CN II, in which $R^1$ is selected from the group consisting of a $C_{1-6}$-alkyl radical, a $C_{2-6}$-alkenyl group or a group of the general formula

IV

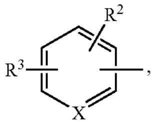, is converted by means of a biologically pure culture of a microorganism which is a member of the strain *Rhodococcus* sp. FZ4, deposited with the Deutsche Sammlung von Mikroorganismen and Zellkulturen GmbH (DSM), Mascheroder Weg 1b, D-38124 Braunschweig on Jul. 11, 2000 and assigned the deposit number 13597, having all the characteristics of said strain and being capable of tolerating an acetonitrile concentration of at least 3M or an enzyme extract obtained from a biologically pure culture of a microorganism which is a member of the strain *Rhodococcus* sp. FZ4, deposited with the Deutsche Sammlung von Mikroorganismen and Zellkulturen GmbH (DSM), Mascheroder Weg 1b, D-38124 Braunschweig on Jul. 11, 2000 and assigned the deposit number 13597, having all the characteristics of said strain and being capable of tolerating an acetonitrile concentration of at least 3M.

2. The method of claim 1, wherein the nitrile is 3-cyanopyridine or acetonitrile.

3. The method of claim 1, wherein the reaction is carried out at a temperature of from 5 to 50° C. and at a pH of from about 5 to 10.

4. The method of claim 2, wherein the reaction is carried out at a temperature of from 5 to 50° C. and at a pH of from about 5 to 10.

5. A method for preparing amides of the general formula $R^1$—$CONH_2$ III wherein $R^1$ is selected from the group consisting of a $C_{1-6}$-alkyl radical, a $C_{2-6}$-alkenyl group or a group of the general formula

IV

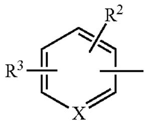

wherein X is a nitrogen atom or —CH═, wherein $R^2$ and $R^3$ are selected from the group consisting of a hydrogen atom, a halogen atom, a $C_{1-6}$-alkyl group or a $C_{2-6}$-alkenyl group, wherein said method a nitrile of the general formula $R^1$—CN II, in which $R^1$ is selected from the group consisting of a $C_{1-6}$-alkyl radical, a $C_{2-6}$-alkenyl group or a group of the general formula

IV

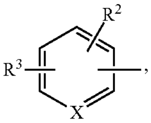, is converted by means of a cell extract derived from a biologically pure culture of a microorganism which is a member of the strain *Rhodococcus* sp. FZ4, deposited with the Deutsche Sammlung von Mikroorganismen and Zellkulturen GmbH (DSM), Mascheroder Weg 1b, D-38124 Braunschweig on Jul. 11, 2000 and assigned the deposit number 13597, having all the characteristics of said strain and being capable of tolerating an acetonitrile concentration of at least 3M or an enzyme extract obtained from a biologically pure culture of a microorganism which is a member of the strain *Rhodococcus* sp. FZ4, deposited with the Deutsche Sammlung von Mikroorganismen and Zellkulturen GmbH (DSM), Mascheroder Weg 1b, D-38124 Braunschweig on Jul. 11, 2000 and assigned the deposit number 13597, having all the characteristics of said strain and being capable of tolerating an acetonitrile concentration of at least 3M.

6. The method of claim 5, wherein the nitrile is 3-cyanopyridine or acetonitrile.

7. The method of claim 5, wherein the reaction is carried out at a temperature of from 5 to 50° C. and at a pH of from about 5 to 10.

8. The method of claim 6, wherein the reaction is carried out at a temperature of from 5 to 50° C. and at a pH of from about 5 to 10.

9. A method for preparing amides of the general formula $R^1$—$CONH_2$ III wherein $R^1$ is selected from the group consisting of a $C_{1-6}$-alkyl radical, a $C_{2-6}$-alkenyl group or a group of the general formula

IV

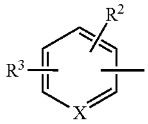

wherein X is a nitrogen atom or —CH═, wherein $R^2$ and $R^3$ are selected from the group consisting of a hydrogen atom, a halogen atom, a $C_{1-6}$-alkyl group or a $C_{2-6}$-alkenyl group, wherein said method a nitrile of the general formula $R^1$—CN II, in which $R^1$ is selected from the group consisting of a $C_{1-6}$-alkyl radical, a $C_{2-6}$-alkenyl group or a group of the general formula

IV

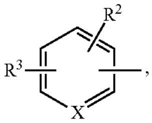, is converted by means of the nitrile hydratase obtainable from a biologically pure culture of a microorganism which is a member of the strain *Rhodococcus* sp. FZ4, deposited with the Deutsche Sammlung von Mikroorganismen and Zellkulturen GmbH (DSM), Mascheroder Weg 1b, D-38124 Braunschweig on Jul. 11, 2000 and assigned the deposit number 13597, having all the characteristics of said strain and being capable of tolerating an acetonitrile concentration of at least 3M or an enzyme extract obtained from a biologically pure culture of a microorganism which is a member of the strain *Rhodococcus* sp. FZ4, deposited with the Deutsche Sammlung von Mikroorganismen and Zellkulturen GmbH (DSM), Mascheroder Weg 1b, D-38124 Braunschweig on Jul. 11, 2000 and assigned the deposit number 13597, having all the characteristics of said strain and being capable of tolerating an acetonitrile concentration of at least 3M.

10. The method of claim 9, wherein the nitrile is 3-cyanopyridine or acetonitrile.

11. The method of claim 9, wherein the reaction is carried out at a temperature of from 5 to 50° C. and at a pH of from about 5 to 10.

12. The method of claim 10, wherein the reaction is carried out at a temperature of from 5 to 50° C. and at a pH of from about 5 to 10.

13. A method for removing acetonitrile from waste comprising acetonitrile wherein said method comprises contacting said waste with a biologically pure culture of a microorganism which is a member of the strain *Rhodococcus* sp. FZ4, deposited with the Deutsche Sammlung von Mikroorganismen and Zellkulturen GmbH (DSM), Mascheroder Weg 1b, D-38124 Braunschweig on Jul. 11, 2000 and assigned the deposit number 13597, having all the characteristics of said strain and being capable of tolerating an acetonitrile concentration of at least 3M or an enzyme extract obtained from a biologically pure culture of a microorganism which is a member of the strain *Rhodococcus* sp. FZ4, deposited with the Deutsche Sammlung von Mikroorganismen and Zellkulturen GmbH (DSM), Mascheroder Weg 1b, D-38124 Braunschweig on Jul. 11, 2000 and assigned the deposit number 13597, having all the characteristics of said strain and being capable of tolerating an acetonitrile concentration of at least 3M under conditions whereby said acetonitrile is removed.

14. A method for removing acetonitrile from waste comprising acetonitrile wherein said method comprises contacting said waste with a cell extract derived from a biologically pure culture of a microorganism which is a member of the strain *Rhodococcus* sp. FZ4, deposited with the Deutsche Sammlung von Mikroorganismen and Zellkulturen GmbH (DSM), Mascheroder Weg 1b, D-38124 Braunschweig on Jul. 11, 2000 and assigned the deposit number 13597, having all the characteristics of said strain and being capable of tolerating an acetonitrile concentration of at least 3M or an enzyme extract obtained from a biologically pure culture of a microorganism which is a member of the strain *Rhodococcus* sp. FZ4, deposited with the Deutsche Sammlung von Mikroorganismen and Zellkulturen GmbH (DSM), Mascheroder Weg 1b, D-38124 Braunschweig on Jul. 11, 2000 and assigned the deposit number 13597, having all the characteristics of said strain and being capable of tolerating an acetonitrile concentration of at least 3M under conditions whereby said acetonitrile is removed.

* * * * *